United States Patent [19]

Giorgetti et al.

[11] Patent Number: 5,124,144
[45] Date of Patent: Jun. 23, 1992

[54] ORALLY ADMINISTERED PHARMACEUTICAL COMPOSITION FOR USE IN GASTROINTESTINAL WASHES, IN PARTICULAR FOR DIAGNOSTIC USE, OR AS A CATHARTIC LAXATIVE

[75] Inventors: Enzo Giorgetti, Milan; Virginio Castagnola, deceased, late of Milan, by Constanza Poma, Laura Castagnola, Marco Castagnola, heirs; Giuliano Frigerio, Bresso, all of Italy

[73] Assignee: Giuliani S.p.A., Milan, Italy

[21] Appl. No.: 508,251

[22] Filed: Apr. 11, 1990

[30] Foreign Application Priority Data

Apr. 17, 1989 [IT] Italy .................. 20168 A/89

[51] Int. Cl.5 .............. A61K 47/34; A61K 9/16; A61K 9/08; A61K 33/00
[52] U.S. Cl. .................. 424/78.01; 424/486; 424/501; 424/679; 424/78.38; 424/680; 424/717; 514/867; 514/892; 514/921; 514/974
[58] Field of Search ............ 424/78, 486, 501, 679; 514/892, 867, 921, 974

[56] References Cited

U.S. PATENT DOCUMENTS 3,897,550 7/1975 Reynolds .................. 424/679
4,761,274 8/1988 Denick, Jr. et al. ........... 514/974
4,942,042 7/1990 Bhargava et al. ............. 424/679

Primary Examiner—Thurman K. Page
Assistant Examiner—E. J. Webman
Attorney, Agent, or Firm—Hedman, Gibson & Costigan

[57] ABSTRACT

The invention provides an orally administered pharmaceutical composition for use in gastrointestinal washes, particularly for diagnostic use, or as a cathartic laxative, of the type containing polyethyleneglycol, anhydrous sodium sulphate, sodium bicarbonate, sodium chloride and potassium chloride, characterized by also containing the following components: saccharin, acesulfame-K and a flavoring chosen from the following: mandarin, fresh fruit flavoring.

6 Claims, No Drawings

ORALLY ADMINISTERED PHARMACEUTICAL COMPOSITION FOR USE IN GASTROINTESTINAL WASHES, IN PARTICULAR FOR DIAGNOSTIC USE, OR AS A CATHARTIC LAXATIVE

BACKGROUND OF THE INVENTION

Preparations consisting of aqueous solutions of polyethyleneglycol and electrolytes, such as, anhydrous sodium sulfate, sodium bicarbonate, sodium chloride and potassium chloride are known for use in the rapid washing of the colon for diagnostic purposes. When a powerful gastrointestinal wash is required, this preparation is generally administered orally in a quantity of about four liters, the composition per liter being typically the following: polyethyleneglycol 59 g, sodium sulphate 5.68 g, sodium bicarbonate 1.68 g, sodium chloride 1.46 g, potassium chloride 0.745 g and water to make up to 1 liter.

The advantages of using such preparations are a drastic reduction in the wash time (from 2-3 days to 4-5 hours) and the minimization of water and electrolyte losses.

These represent substantial improvements which derive from two essential characteristics of the preparation, namely its isoosmoticity with the physiological liquids, and the balance of the ionic species in solution, so as to compensate the transport mechanisms which regulate gastrointestinal absorption.

These characteristics result in substantial isotonicity between the preparation and the intra and extracellular fluids at the tissues of the digestive tube walls.

In developing such preparations, this isotonicity was obtained by experimentally balancing the ionic species in solution, and also by calculating the osmotic pressure and evaluating the mechanisms which control transfer at the gastrointestinal walls.

A serious drawback of these known preparations is, however, their decidedly unpleasant bitter, saline taste, which in the more sensitive patients can lead to vomiting, thereby preventing ingestion. However, the requirement of solution isotonicity, which as stated is necessary to obtain the aforesaid advantages, does not generally allow, or at least makes very problematic, the introduction of water-soluble adjuvants into known formulations as they would alter this isotonicity. In this respect, some commercial preparations expressly state that taste correctors must not be added on diluting the preparation.

Furthermore, in the aforesaid preparations of the known art it is not opportune to add appreciable quantities of substances which can be fermented by the intestinal flora, because gas could form which could be extremely dangerous in cases of colonoscopy with electrocautery. Neither is it possible to introduce water-soluble substances in quantities such as to alter the osmotic conditions of the solution. The effect would be to lose the effectiveness and tolerance of the preparation. Neither is it possible to introduce electrolytes which would significantly alter the concentration of one or more ionic species present in the preparation. The result would be similar to that produced by altering the osmolarity. A further impediment to adding water-soluble substances for taste correction, in particular edulcorators, is that even the most common natural sweeteners such as saccharose, fructose, glucose and sorbitol would cause fermentation of the preparation and a change in its osmolarity.

For other edulcorators such as synthetic sweeteners there is a further problem in addition to the aforesaid general problems, namely the problem of toxicity at high doses, so that the acceptable daily dose (ADD) must be taken into account. Remembering that the preparation of the known art is taken orally in a quantity of four liters of solution per unit of administration, practically all known synthetic edulcorators would have to be administered in effective doses which are incompatible with the ADD fixed by regulations.

According to the present invention it has now been found possible to provide a preparation for oral use of the aforesaid kind which while being unaltered in terms of its capacity for rapid gastrointestinal washing is of substantially changed taste in the sense of being in fact pleasant for the patient.

According to a further aspect of the present invention, it has also been found that this preparation not only performs an effective gastrointestinal wash but at smaller doses demonstrates effective activity as a cathartic laxative.

The invention, which produces the aforesaid surprising effects and other advantages which will be apparent hereinafter, comprises an orally administered pharmaceutical composition for use in gastrointestinal washes, particularly for diagnostic use, or as a cathartic laxative of the type containing polyethyleneglycol, anhydrous sodium sulphate, sodium bicarbonate, sodium chloride and potassium chloride, characterised by also containing the following components: saccharin, acesulfame-K and a flavoring chosen from the following: mandarin, fresh fruit flavourings. According to a further embodiment, the composition of the present invention also contains sodium cyclamate.

According to the invention, the addition of said components in the suitable concentration ranges hereinafter defined has been found not to alter the isotonicity of the final solution, as is necessary for correct and satisfactory gastrointestinal washing within the short time required, i.e. a few hours. It has also been found not to induce the other feared effects, i.e. fermentation and ionic unbalance, and is able to maintain the composition ADD within acceptable values. These effects are combined with a pleasant taste such as to obviate all problems of its administration to the patient.

The characteristics and advantages of the invention will be more apparent from the following non-limiting practical examples.

EXAMPLE 1

Granulate of mandarin flavor. (Cathartic laxative or gastrointestinal wash)

This is a granular composition divided into single-dose fractions to be dissolved at the time of use in a determined volume of tap water.

Formula for one dose to make 0.5 liters of extemporaneous solution:

|  | Cathartic laxative maximum dose 1 l | Gastrointestinal wash maximum dose 4 l |
| --- | --- | --- |
| PA1 polyethylene glycol (3000-4000) |  | 29.5 g ± 20% |
| PA2 anhydrous sodium sulphate | 2.843 g ± 10% |  |
| PA3 sodium bicarbonate | 0.843 g ± 10% |  |

-continued

|  | Cathartic laxative maximum dose 1 l | Gastrointestinal wash maximum dose 4 l |
| --- | --- | --- |
| PA4 sodium chloride | 0.733 g ± 10% | |
| PA5 potassium chloride | 0.371 g ± 10% | |
| SC1 saccharin | 0.010–0.320 g | 0.010–0.025 g |
| SC2 sodium cyclamate | 0.000–0.100 g | 0.050–0.100 g |
| SC3 acesulfame-K | 0.040–0.160 g | 0.040–0.080 g |
| SC4 water-dispersable mandarin flavoring of food grade (powder and/or liquid, yield ≧ 1:500) | ≦1.000 g according to concentration | |

Preparation Method

A—weigh out the components in the proportions indicated by the dose formula according to the size of the batch to be prepared.

B—Place the component PA1 in a suitable capacity stainless steel powder mixer after forcing through a 10–20 mesh stainless steel screen.

C—Add component PA2 after forcing through a 20–30 mesh stainless steel screen.

D—Add components PA3, PA4, PA5, SC1, SC2, SC3 and SC4 (only if powder) after forcing them through a 30–40 mesh stainless steel screen and mixing them together.

E—Mix for 15–30 minutes according to the operation of the mixer used.

F—If component SC4 is used totally or partially in liquid form, spray it onto the other components under mixing, using a normal spray device operated at very low pressure.

G—Divide the mixture into single-dose fractions e.g. sachets or bottles) by means of a common dispenser with a dispensing accuracy of ±5 of the theoretical for each fraction.

H—Make up a final pack containing the necessary number of fractions to satisfy the pharmaceutical and commercial requirements of the preparation.

EXAMPLE 2

Granulates of various fresh fruit flavors.

Example 1 is repeated with the exception of component SC4. In its place different liquid or powder fresh fruit flavorings of food grade having a yield equal to or greater than 1:500 are used indiscriminately, either alone or in various combinations, in the quantities indicated in the formula of Example 1. Similar results are obtained with all fruit flavorings which provide a fresh fruit taste (but not so-called dry fruits such as walnuts, hazel nuts, and peanuts) even of different categories, such as:

Classical fruits (e.g. cherry, plum, apple and apricot)
Citrus fruits (e.g. lemon and orange)
Wild fruits (e.g. strawberry, raspberry, and bilberry)
Tropical fruits (e.g. grapefruit, pineapple and banana)

EXAMPLE 3

Concentrated solution of special mandarin flavor. (Cathartic laxative or gastrointestinal wash)

This is a concentrated solution divided into single-dose fractions to be diluted at the time of use with tap water to a given final volume.

Formula for one dose to make 0.5 liters of extemporaneous solution:

|  | Cathartic laxative maximum dose 1 l | Gastrointestinal wash maximum dose 4 l |
| --- | --- | --- |
| PA1 polyethylene glycol (3000–4000) | 29.5 g ± 20% | |
| PA2 anhydrous sodium sulphate | 2.843 g ± 10% | |
| PA3 sodium bicarbonate | 0.843 g ± 10% | |
| PA4 sodium chloride | 0.733 g ± 10% | |
| PA5 potassium chloride | 0.371 g ± 10% | |
| SC1 saccharin | 0.010–0.320 g | 0.010–0.025 g |
| SC2 sodium cyclamate | 0.000–0.100 g | 0.050–0.100 g |
| SC3 acesulfame-K | 0.040–0.160 g | 0.040–0.080 g |
| SC4 water-dispersable mandarin flavoring of food grade (powder and/or liquid, yield ≧ 1:1000) | ≦0.500 g | |
| SC5 ca. 50% solution of equal amounts of sodium salts of methyl, ethyl and propyl esters of p-hydroxybenzoic acid stabilized with NaOH and sodium benzoate | 0.5–0.6 g | |
| VSI tap water to make up to | 250 ml | |

Preparation Method

A—Weigh out the components in the proportions indicated by the dose formula according to the size of the batch to be prepared.

B—Place the component VSI in a suitable capacity stainless steel dissolving vessel fitted with a mechanical stirrer and commence stirring.

C—While stirring, add all the other components in the reverse order to that indicated by the dose formula.

D—Continue stirring until all the components have dissolved (clear solution), i.e. for about 30 minutes.

E—Divide the solution into single-dose fractions (e.g. bottles or sachets) by means of a common dispenser with a dispensing accuracy of ±5% of the theoretical for each fraction.

F—Make up a final pack containing the necessary number of fractions to satisfy the pharmaceutical and commercial requirements of the preparation.

EXAMPLE 4

Concentrated solutions, various fresh fruit flavors.

Example 3 is repeated in its entirety except with regard to component SC4.

In its place different liquid or powder fresh fruit flavorings of food grade having a yield equal to or greater than 1:1000 are used indiscriminately, either alone or in various combinations, in the quantities indicated in the formula of Example 3. Similar results are obtained with all fruit flavourings which provide a fresh fruit taste (but not so-called dry fruits such as walnuts, hazel nuts and peanuts) even of different categories, such as:

Classical fruits (e.g. cherry, plum, apple and apricot)
Citrus fruits (e.g. lemon and orange)
Wild fruits (e.g. strawberry, raspberry and bilberry)
Tropical fruits (e.g. grapefruit, pineapple and banana).

EXAMPLE 5

Ready-for-use solution of special mandarin flavor. This is a ready-for-use solution divided into single-dose fractions to be used according to the indicated posology. Formula for a 0.5 l dose.

|  | Cathartic laxative maximum dose 1 l | Gastrointestinal wash maximum dose 4 l |
| --- | --- | --- |
| PA1 polyethylene glycol (3000-4000) | 29.5 g ± 20% | |
| PA2 anhydrous sodium sulphate | 2.843 g ± 10% | |
| PA3 sodium bicarbonate | 0.843 g ± 10% | |
| PA4 sodium chloride | 0.733 g ± 10% | |
| PA5 potassium chloride | 0.371 g ± 10% | |
| SC1 saccharin | 0.010-0.320 g | 0.010-0.025 g |
| SC2 sodium cyclamate | 0.000-0.100 g | 0.050-0.100 g |
| SC3 acesulfame-K | 0.040-0.160 g | 0.040-0.080 g |
| SC4 water-dispersable mandarin flavoring of food grade (powder and/or liquid, yield ≧ 1:2000) | ≦0.250 g | |
| SC5 ca. 50% solution of equal amounts of the sodium salts of methyl, ethyl and propyl esters of p-hydroxybenzoic acid stabilized with NaOH and sodium benzoate | | 0.6-1.2 g |
| VSI tap water to make up to | 500 ml | |

Preparation Method

A—Weigh out the components in the proportions indicated by the dose formula according to the size of the batch to be prepared.

B—Place the component VSI in a suitable capacity stainless steel dissolving vessel fitted with a mechanical stirrer and commence stirring.

C—While stirring, add all the other components in the reverse order to that indicated by the dose formula.

D—Continue stirring until all the components have dissolved (clear solution), i.e. for about 30 minutes.

E—Divide the solution into single-dose fractions (e.g. bottles and sachets) by means of a common dispenser with a dispensing accuracy of ±5% of the theoretical for each fraction.

F—Make up a final pack containing the necessary number of fractions to satisfy the pharmaceutical and commercial requirements of the preparation.

EXAMPLE 6

Ready-for-use solutions of various fresh fruit flavors.

Example 5 is repeated in its entirety except with regard to component SC4.

In its place different liquid or powder fresh fruit flavorings of food grade having a yield equal to or greater than 1:2000 are used indiscriminately, either alone or in various combinations, in the quantities indicated in the formula of Example 5. Similar results are obtained with all fruit flavourings which provide a fresh fruit taste (but not so-called dry fruits such as walnuts, hazel nuts and peanut) even of different categories, such as:

Classical fruits (e.g. cherry, plum, apple and apricot)

Citrus fruits - tangerine excepted - (e.g. lemon and orange)

Wild fruits (e.g. strawberry, raspberry and bilberry)

Tropical fruits (e.g. grapefruit, pineapple and banana).

The compositions of the invention were tested experimentally. The following were evaluated in each case: any production of effects such as fermentation; instability at pH 7.5; the maintaining of osmolarity within the desired limits, i.e. within the range of 237-321 m osmoles liter; ionic unbalance; ADD 70 in one liter (use as cathartic laxative); ADD 70 in four liters (use as gastrointestinal wash solution).

Total absence of negative effects was found in all cases. The compositions were then administered to patients, who evaluated their taste on a 0-10 scale ranging from very bad to very good. All the experimental values are given in the following table.

TABLE

| Test No. | Overall evaluation | Composition of the invention: components added to the basic formulation | g/l | Taste | Fermentation | Stability at pH 7.5 | Osmolarity | Ionic unbalance | ADD 70 1 lit mean values | ADD 70 4 lit mean values |
| --- | --- | --- | --- | --- | --- | --- | --- | --- | --- | --- |
| 1 | Acceptable | Saccharin<br>Acesulfame K<br>Fresh fruit flavoring | 0.175<br>0.315<br>according to concentration | 4.8 | No | Yes | Conforms | No | 0.75 | 3 |
| 2 | Acceptable | Saccharin<br>Acesulfame K<br>Mandarin flavoring | 0.175<br>0.315<br>according to concentration | 5.6 | No | Yes | Conforms | No | 0.75 | 3 |
| 3 | Acceptable | Saccharin<br>Sodium cyclamate<br>Acesulfame K<br>Fresh fruit flavoring | 0.022<br>0.096<br>0.078<br>according to concentration | 4.48 | No | Yes | Conforms | No | 0.125 | 0.5 |
| 4 | Acceptable | Saccharin<br>Sodium cyclamate<br>Acesulfame K<br>Mandarin flavoring | 0.022<br>0.096<br>0.078<br>according to concentration | 5.4 | No | Yes | Conforms | No | 0.125 | 0.5 |
| 5 | Acceptable | Saccharin<br>Sodium cyclamate<br>Acesulfame K<br>Fresh fruit flavoring | 0.045<br>0.192<br>0.157<br>according to concentration | 5.17 | No | Yes | Conforms | No | 0.125 | 1 |
| 6 | High | Saccharin<br>Sodium cyclamate<br>Acesulfame K<br>Mandarin flavoring | 0.045<br>0.192<br>0.157<br>according to concentration | 7.93 | No | Yes | Conforms | No | 0.125 | 1 |

From the table data, it can be seen that the invention enables preparations to be prepared which effectively solve the initially stated technical problem relative to the unacceptable taste of the composition, while completely avoiding the feared negative effects of the known art deriving from the addition of further components to the basic formulation.

According to the invention it has also been found that at the aforestated lower doses the formulated compositions have a further effective use as a cathartic laxative, this not being of the known art.

It is claimed:

1. An orally administered pharmaceutical composition for use in gastrointestinal washes, particularly for diagnostic use, or as a cathartic laxative, comprising per 0.5 liter of an aqueous solution:

| | |
|---|---|
| polyethyleneglycol (3000–4000) | 29.5 g ± 20% |
| anhydrous sodium sulfate | 2.843 g ± 10% |
| sodium bicarbonate | 0.843 g ± 10% |
| sodium chloride | 0.733 g ± 10% |
| potassium chloride | 0.371 g ± 10% |
| saccharin | 0.010–0.320 g |
| acesulfame-K | 0.040–0.160 g |
| flavoring | ≦1.000 g. |

2. The composition as claimed in claim 1 further comprising sodium cyclamate.

3. The composition as claimed in claim 2, comprising per 0.5 liter of an aqueous solution:

| | |
|---|---|
| polyethyleneglycol (3000–4000) | 29.5 g ± 20% |
| anhydrous sodium sulfate | 2.843 g ± 10% |
| sodium bicarbonate | 0.843 g ± 10% |
| sodium chloride | 0.733 g ± 10% |
| potassium chloride | 0.371 g ± 10% |
| saccharin | 0.010–0.320 g |
| sodium cyclamate | 0.01–0.100 g |
| acesulfame-K | 0.040–0.160 g. |

4. The composition as claimed in claim 2, adapted for use as a gastrointestinal wash to be administered in a maximum dose of four liters of solution, said composition comprising per 0.5 liter of an aqueous solution:

| | |
|---|---|
| polyethyleneglycol (3000–4000) | 29.5 g ± 20% |
| anhydrous sodium sulfate | 2.843 g ± 10% |
| sodium bicarbonate | 0.843 g ± 10% |
| sodium chloride | 0.733 g ± 10% |
| potassium chloride | 0.371 g ± 10% |
| saccharin | 0.010–0.025 g |
| sodium cyclamate | 0.050–0.100 g |
| acesulfame-K | 0.040–0.080 g |
| flavoring | ≦1.000 g |

5. The composition as claimed in claim 1 adapted for use as a cathartic laxative to be administered in a maximum dose of one liter of solution, said composition comprising per 0.5 liter of an aqueous solution:

| | |
|---|---|
| polyethyleneglycol (3000–4000) | 29.5 g ± 20% |
| anhydrous sodium sulfate | 2.843 g ± 10% |
| sodium bicarbonate | 0.843 g ± 10% |
| sodium chloride | 0.733 g ± 10% |
| potassium chloride | 0.371 g ± 10% |
| saccharin | 0.010–0.320 g |
| acesulfame-K | 0.040–0.160 g |
| flavoring | ≦1.000 g. |

6. A method of obtaining a laxative effect on a warm blooded animal comprising administering to said warm blooded animal a laxative effective amount of the composition of claim 1.

* * * * *